(12) United States Patent
Aida et al.

(10) Patent No.: US 7,132,391 B2
(45) Date of Patent: Nov. 7, 2006

(54) ETHERS OF 2,2,4-TRIMETHYLPENTANE-1,3-DIOL AS FRAGRANCE MATERIALS

(75) Inventors: Takashi Aida, Chigashaki (JP); Andrew T. Lupo, Emerson, NJ (US); Hiroyuki Matsuda, Kanagawa (JP)

(73) Assignee: Takasago International Corporation, Tokyo (JP)

( * ) Notice: Subject to any disclaimer, the term of this patent is extended or adjusted under 35 U.S.C. 154(b) by 301 days.

(21) Appl. No.: 10/193,024

(22) Filed: Jul. 10, 2002

(65) Prior Publication Data

US 2004/0014633 A1 Jan. 22, 2004

(51) Int. Cl.
*A61Q 13/00* (2006.01)

(52) U.S. Cl. .................. 512/25; 568/579; 568/670; 568/671; 568/672; 568/673; 568/675; 568/700; 568/822; 568/823; 568/840; 568/891

(58) Field of Classification Search .......... 512/25; 568/579, 670, 671, 672, 673, 675, 700, 822, 568/823, 840, 891
See application file for complete search history.

(56) References Cited

U.S. PATENT DOCUMENTS

| 3,287,420 A | 11/1966 | Johnson et al. |
| 3,409,657 A | 11/1968 | Blood et al. |

FOREIGN PATENT DOCUMENTS

| JP | 2001271087 | 10/2001 |
| WO | WO 95/21606 | 8/1995 |

OTHER PUBLICATIONS

Jung et al. "Oxidation of ethers via hydride abstraction: a new procedure for selective oxidation of primary, secondary diols at the secondary position," Journal of the American Chemical Society, 98(24), 7882-4(1976).*
Journal of the American Chemical Society; 98:24; Nov. 24, 1976; "Oxidation of Ethers via Hydride Abstraction: A New Procedure for Selective Oxidation of Primary, Secondary Diols at the Secondary Position"; pp. 7882-7884.
European Search Report 03291711.4-2103.

* cited by examiner

*Primary Examiner*—Monique T. Cole
(74) *Attorney, Agent, or Firm*—Darby & Darby

(57) ABSTRACT

An alkyl gycol ether having the following formula

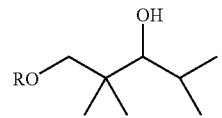

wherein R is a $C_1$–$C_7$ saturated, unsaturated, straight-chain or branched, acyclic or cyclic alkyl group, is useful as a fragrance material in perfumes, cosmetics, consumer products, and the like. When R is a saturated, straight-chain or branched, acyclic or cyclic alkyl group, these compounds are especially stable when used as fragrance materials in bleach containing products.

23 Claims, No Drawings

ETHERS OF 2,2,4-TRIMETHYLPENTANE-1,3-DIOL AS FRAGRANCE MATERIALS

BACKGROUND OF THE INVENTION

The present invention relates to novel alkyl ethers of 2,2,4-trimethylpentane-1,3-diol. The present invention further relates to the use of these compounds as fragrance materials or as fragrance composition additives in perfumes, cosmetics, consumer products, and the like.

International Publication Number WO 95/21606 discloses 2,2,4-trimethyl-penten-1-yl ester compounds useful as fragrance and flavor compositions. The generic structure of these compounds are shown in general formulas (1) and (2) below.

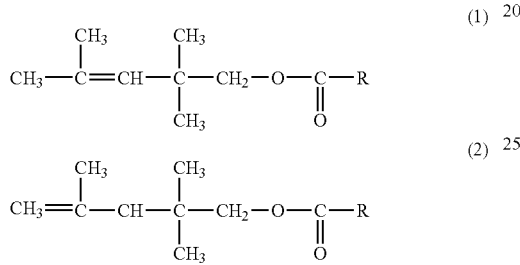

wherein R is H, or a substituted or unsubstituted $C_1$–$C_6$ alkyl, $C_2$–$C_6$ alkenyl, $C_6$–$C_{12}$ aryl, or $C_7$–$C_{18}$ alkylaryl.

U.S. Pat. No. 4,150,007 relates to the use of an adduct of ethylene oxide and 2,2,4-trimethylpentane-1,3-diol as a reactive diluent in water-bourne coatings. The diol-ethylene oxide adducts are a mixture of components having the general formula (3)

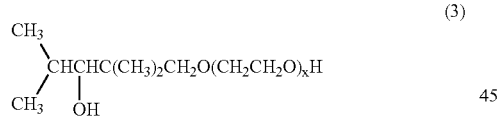

wherein x is an integer from 0 to 3.

U.S. Pat. No. 5,763,144 discloses a glycidyl ether having formula (4) as shown below.

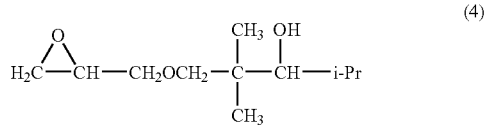

These compounds are useful as intermediates in the preparation of photographic stabilizers.

The reaction of ROTiCl3 with R1CH(OR2)2 is disclosed in *C.R. Acad. Sci., Ser. C* (P. Mastagli, D. Gibert, vol. 227, no. 9, pages 347–249, 1973). One specific product of this reaction is CAS Registry No. [50598-30-6], identified below in formula (5).

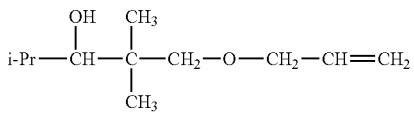

This report discusses only the preparation of this material as an example of the utility of the synthetic method studied. No further utility is disclosed.

Synthetic chemical compounds which are able to provide a desirable aroma are of great importance to the fragrance industry. Many of the natural materials which impart such aromas to fragrance compositions are often expensive and of variable quality. Furthermore, such materials are often times unavailable. Accordingly, efforts have been made to find synthetic substitutes for these natural materials. Many of these efforts, however, have resulted in compounds which possess only a small degree of fragrance character, or contribute an undesired odor to the fragrance composition.

OBJECTS AND SUMMARY OF THE INVENTION

It is an object of the present invention to provide novel ethers of 2,2,4-trimethylpentane-1,3-diol.

It is a further object of the present invention to provide a fragrance composition having ethers of 2,2,4-trimethylpentane-1,3-diol.

It is another object of the present invention to provide a method of using ethers of 2,2,4-trimethylpentane-1,3-diol as fragrance materials.

It is still a further object of the present invention to provide a method of making novel ethers of 2,2,4-trimethylpentane-1,3-diol.

Briefly stated, the present invention provides an alkyl gycol ether having the following formula

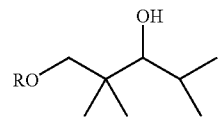

wherein R is a $C_1$–$C_7$ saturated, unsaturated, straight-chain or branched, acyclic or cyclic alkyl group, is useful as a fragrance material in perfumes, cosmetics, consumer products, and the like. When R is a saturated, straight-chain or branched, acyclic or cyclic alkyl group, these compounds are especially stable when used as fragrance materials in bleach containing products.

According to an embodiment of the present invention, there is provided a compound having the formula

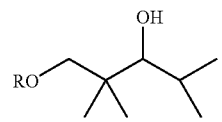

wherein R is a $C_1$–$C_7$ saturated, unsaturated, straight-chain or branched, acyclic or cyclic alkyl group, provided that R is not a 2-propenyl group.

According to a further embodiment of the present invention, there is provided a fragrance composition comprising a compound having the formula

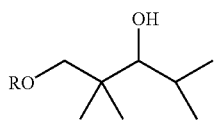

wherein R is a $C_1$–$C_7$ saturated, unsaturated, straight-chain or branched, acyclic or cyclic alkyl group, and a suitable carrier.

According to another embodiment of the present invention, there is provided a method of adding fragrance to a composition, comprising adding a suitable amount of a compound having the formula

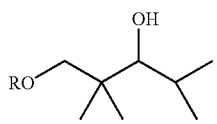

wherein R is a $C_1$–$C_7$ saturated, unsaturated, straight-chain or branched, acyclic or cyclic alkyl group to a composition in need thereof.

According to another feature of the present invention, there is provided a method for making a compound having the formula

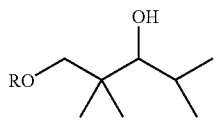

comprising contacting a 2,2,4-trimethyl-1,3-diol with a compound having the formula R—X, wherein X is any suitable leaving group, in the presence of a base at a temperature suitable to cause a reaction therebetween.

DETAILED DESCRIPTION OF THE INVENTION

As noted above, the 2,2,4-trimethylpentane-1,3-diol compounds of the present invention include compounds of the following formula (6)

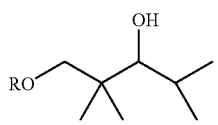

(6)

wherein R is a $C_1$–$C_7$ alkyl group.

An "alkyl group" is defined as being a saturated, unsaturated, straight-chained or branched, acyclic or cyclic hydrocarbon moiety. Specific examples of an "alkyl group" include straight-chained, saturated hydrocarbon groups, such as methyl, ethyl, propyl, and butyl; branched, saturated hydrocarbon groups, such as isobutyl, isopropyl, t-butyl, and neopentyl; straight-chained unsaturated hydrocarbon groups such as n-pentyl-3-ene; branched unsaturated hydrocarbon groups, such as prenyl, 2-methylbutyl-2-ene; cyclic saturated hydrocarbon groups, such as 1-methyl cyclohexane; and cyclic unsaturated hydrocarbon groups, such as 1-methyl, cyclohexene.

Specific examples of compounds useful as fragrance materials according to the present invention include formulas (7), (8), (9), and (10) as shown below.

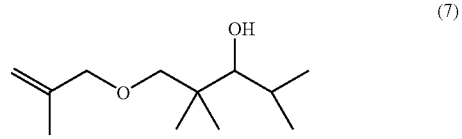

(7)

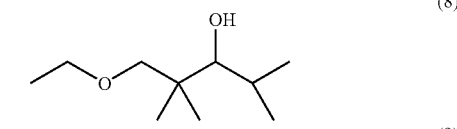

(8)

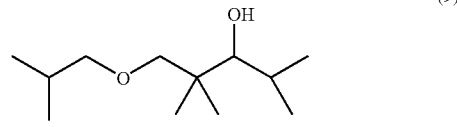

(9)

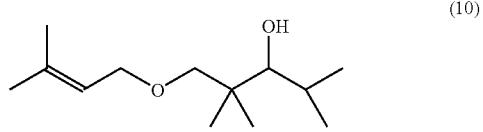

(10)

The above compounds are useful in creating fragrances in a wide range of perfume, cosmetic and consumer products. When R is a saturated cyclic or acyclic alkyl group, these materials are particularly useful for fragrancing bleach containing products. Such compounds have been shown to be adequately chemically stable in a bleach stability test.

The compounds of the present invention are made according to method of the following Scheme 1.

SCHEME I

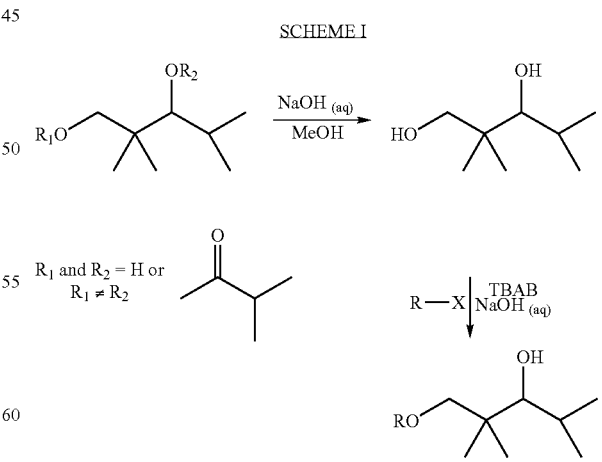

In Scheme I, X is any suitable leaving group, preferably a halide, even more preferably a chlorine or bromine atom, R is a $C_1$–$C_7$ alkyl group, as previously defined, and TBAB is tetrabutyl ammonium bromide.

While not limited to the following, the present invention is illustrated by the following examples.

The ethers of 2,2,4-trimethylpentane-1,3-diol represented by the general formula (6) of the present invention can be used alone as a scent component, or one or more can be used in combination. Furthermore, one or more of the ethers of 2,2,4-trimethylpentane-1,3-diol of the present invention represented by the general formula (6) and one or more fragrance materials that are known to those skilled in the art can be mixed and used as a fragrance composition. When preparing a fragrance composition, the compounds of the present invention, ethers of 2,2,4-trimethylpentane-1,3-diol represented by the general formula (6), are normally incorporated at from about 0.01 to about 50 weight %, and preferably from about 0.1 to about 20 weight %, in said fragrance composition; the exact incorporation level being dependant upon the olfactive objective or fragrance type desired.

The ethers of 2,2,4-trimethylpentane-1,3-diol of the present invention represented by the general formula (6) are used in various perfume products and sanitation products that require the addition of fragrances. Not only does the present invention show high stability in ordinal base materials, but the saturated ethers of 2,2,4-trimethylpentane-1,3-diol of the present invention represented by the general formula (6) can be added a) without resulting in the loss of the activity of bleaching components, such as hypochlorites, percarbonate, perborate, hydrogen peroxide, and, the like, and b) without resulting in decomposition of the ethers of 2,2,4-trimethylpentane-1,3-diol of the present invention.

Stated more specifically, the present invention can be used widely in shampoos, conditioners, perfumes, colognes, hair creams, pomades, hair cosmetic materials, other cosmetic materials or cosmetic cleansers, room fragrance, soaps, dishwashing detergents, laundry detergent, softeners, disinfecting cleaning agents, deodorizing cleaning agents, furniture care materials, disinfectants, bactericidal agents, repellants, bleaching agents, and other sanitation cleaning agents, toothpaste, mouthwash, toilet paper, odor giving agents to aid in the taking of medication, and the like. It is anticipated that the addition of the fragrance composition of the present invention will increase the value of these products."

Hydrolysis of 2,2,4-trimethylpentane-1,3-diol monoisobutyrate:

To a 500 ml flask equipped with a condenser and a thermometer, was added 216.3 g (1.0 mol) of 2,2,4-trimethylpentan-1,3-diol monoisobutyrate and 3 ml of methanol. To this solution was added, drop-wise over 40 minutes, 88 g (1.1 mol) of 50% aqueous NaOH keeping the temperature of the exothermic reaction below 50° C. After an additional 30 minutes the hydrolysis was complete and the reaction mixture was poured into 300 ml of water and extracted with 200 ml of toluene. The organic layer was washed with 30 ml of saturated sodium chloride and evaporated to give 148.1 g of 2,2,4-trimethylpentan-1,3-diol.

EXAMPLE 1

Preparation of 1-(2-methyl-2-propenyloxy)-2,2,4-trimethylpentan-3-ol

To a 1 L flask equipped with a reflux condenser and a thermometer, was added 292.5 g (2.0 mol) of 2,2,4-trimethylpentan-1,3-diol, 352.0 g (4.4 mol) of 50% aqueous NaOH, and 6.45 g (20 mmol) of tetrabutyl ammonium bromide. This mixture was heated in an oil bath and when the reaction mixture reached 50° C., 199.2 g (2.2 mol) of methallyl chloride was added drop-wise over 50 minutes. During the addition, the oil bath temperature was gradually raised to 100° C. and the reaction was continued for an additional 3 hours at 100° C. The reaction mixture was cooled, quenched with 400 ml of water, and extracted twice with 100 ml of toluene. The combined organic layers were washed with 50 ml of saturated ammonium chloride and 50 ml of saturated sodium chloride and evaporated to give 408 g of crude 1-(2-methyl-2-propenyloxy)-2,2,4-trimethylpentan-3-ol.

After reduced pressure distillation (71–80° C., 3 mmHg), 377.1 g (yield 94.1%) of 1-(2-methyl-2-propenyloxy)-2,2,4-trimethylpentan-3-ol was obtained.

$^1$H-NMR (500 MHz, CDCl$_3$, δ) ppm: 0.93 (d, J=6.8 Hz, 3H), 0.95 (s, 3H), 0.96 (s, 3H), 1.02 (d, J=6.9 Hz, 3H), 1.74 (s, 3H), 1.85–1.94 (m, 1H), 3.13 (d, J=3.8 Hz, 1H), 3.19 (d, J=8.7 Hz, 1H), 3.38–3.43 (m, 2H), 3.85 (s, 2H), 4.88 (s, 1H), 4.91 (s, 1H).

IR (film) cm$^{-1}$: 3501, 3077, 2961, 2873, 1657, 1472, 1455, 1414, 1369, 1259, 1171, 1093, 1032, 992, 899. MS (m/e): 200 (M$^+$), 183, 167, 157, 145, 128, 110, 95, 85, 83, 73, 55, 43, 29.

EXAMPLE 2

Preparation of 1-Ethoxy-2,2,4-trimethylpentan-3-ol

Treatment of 2,2,4-trimethylpentan-1,3-diol with ethyl bromide employing the alkylation reaction conditions described above provided 1-ethoxy-2,2,4-trimethylpentan-3-ol in 90.0% yield (313.2 g, b.p.=79–80 C./3.2 mmHg).

$^1$H NMR (500 MHz, CDCl$_3$, δ) ppm: 0.93 (d, J=6.7 Hz, 3H), 0.94 (s, 3H), 0.95 (s, 3H), 1.02 (d, J=7.0 Hz, 3H), 1.19 (t, J=7.0 Hz, 3H), 1.83–1.93 (m, 1H), 3.21 (d, J=8.8 Hz, 1H), 3.25 (br. 1H), 3.30 (d, J=2.3 Hz, 1H), 3.34 (d, J=8.8 Hz, 1H), 3.40–3.48 (m, 2H).

IR (film) cm–1: 3500, 2960, 2870, 1470, 1385, 1110, 990. MS (m/e): 141 (M–43), 131, 113, 83, 73, 56, 43, 29.

EXAMPLE 3

Preparation of 1-(2-methylpropyloxy)-2,2,4-trimethylpentan-3-ol

Treatment of 2,2,4-trimethylpentan-1,3-diol with isobutyl bromide employing the alkylation reaction conditions described above provided 1-(2-methylpropyloxy)-2,2,4-trimethylpentan-3-ol in 88.0% yield (355.5 g, b.p.=81–82 C./2.5 mmHg).

$^1$H NMR (500 MHz, CDCl$_3$, δ) ppm: 0.90 (br.d. J=6.8 Hz, 6H), 0.93 (d, J=6.7 Hz, 3H), 0.94 (s, 3H), 0.96 (s, 3H), 1.02 (d, J=6.9 Hz, 3H), 1.80–1.93 (m, 2H), 3.05 (br. 1H), 3.12–3.19 (m, 2H), 3.20 (d, J=8.8 Hz, 1H), 3.30 (d, J=2.3 Hz, 1H), 3.33 (d, J=8.8 Hz, 1H).

IR (film) cm–1: 3500, 2960, 2870, 1470, 1385, 1110, 990. MS (m/e): 159 (M–43), 147, 113, 103, 83, 73, 57, 41, 29.

EXAMPLE 4

Preparation of 1-(3-methyl-2-butenyloxy)-2,2,4-trimethylpentan-3-ol

Treatment of 2,2,4-trimethylpentan-1,3-diol with prenyl chloride employing the alkylation reaction conditions described above provided 1-(3-methyl-2-butenyloxy)-2,2,4-trimethylpentan-3-ol in 92.0% yield (393.8 g, b.p.=82–84 C./0.8 mmHg).

$^1$H NMR (500 MHz, CDCl$_3$, δ) ppm: 0.93 (d, J=6.9 Hz, 3H), 0.94 (s, 3H), 0.95 (s, 3H), 1.01 (d, J=6.9 Hz, 3H), 1.65 (s, 3H), 1.73 (s, 3H), 1.83–1.92 (m, 1H), 3.19 (d, J=8.8 Hz, 1H), 3.25 (br. 1H), 3.30 (d, J=2.3 Hz, 1H), 3.33 (d, J=8.8 Hz, 1H), 3.93 (d, J=6.8 Hz, 2H), 5.77–5.83 (m, 1H).

IR (film) cm−1: 3500, 2960, 2870, 1675, 1470, 1385, 1080, 990. MS (m/e): 181 (M−33), 154, 145, 131, 112, 103, 85, 69, 55, 41, 27.

Table 1 shows the olfactive descriptions for the compounds obtained in Examples 1–4 above.

| Example | Odor |
| --- | --- |
| 1 | floral, fruity, green |
| 2 | camphoraceous, rosy |
| 3 | floral, woody |
| 4 | floral, fruity |

PREPARATION EXAMPLE 1

Bleach Containing Formulation

When the R group of formula (6) is a saturated cyclic or acyclic alkyl group, these materials are particularly useful for fragrancing bleach containing products.

The bleach stability of saturated ether alcohols were determined as follows. A small amount of the test materials (compounds of the present invention) were added to the "bleach test formula" (see formula below for details) and kept at 40° C. for 4 weeks in a polyethylene vessel. In addition, a blank control is run containing the "bleach test formula" without an aromachemical. Following treatment the samples were evaluated as follows: a) residual NaClO content was analytically determined, and b) olfactive evaluation of the test formula was conducted to determine olfactive stability ("masking effect") of the aromachemical under test.

Table 2 below indicates the results obtained. Residual Cl%=100=(residual Cl of sample)/(residual Cl of blank).

| Sample | Residual Cl % | Masking effect |
| --- | --- | --- |
| Example #2 (compound 6, R = ethyl) | 99.0 | very good |
| Example #3 (compound 6, R = isobutyl) | 98.3 | very good |

| Bleach test formula: | |
| --- | --- |
| Component | Wt % |
| NaClO solution | 5.0 (as available chlorine) |
| NaOH | 1.0 |
| Surfactant | 3.0 |
| Aroma chemical | 0.3 |
| stilled water | Q.S. |
| Total | 100.0 |

PREPARATION EXAMPLE 2

Fragrance Composition

Fragrance formula using a compound of the present invention:

| Ingredient | Amount (wt. %) |
| --- | --- |
| ambretone | 4.5 |
| tricyclodecenyl butyrate | 0.4 |
| tricyclodecenyl acetate | 0.3 |
| DH myrcenol | 0.4 |
| ethyl cinnamate | 0.4 |
| Example #1 (compound 6, R methallyl) | 12.5 |
| geranyl formate | 0.3 |
| hexyl cinnamic aldehyde | 3.5 |
| Musk T | 40.0 |
| Phenyl propyl alcohol | 0.2 |
| phenoxy ethyl isobutyrate | 2.0 |
| undecalactone, gamma | 10.5 |
| 2-tert-butylcyclohexyl acetate | 25.0 |

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. A compound having the formula

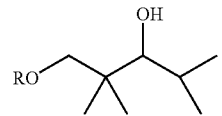

wherein R is a C$_3$–C$_7$ unsaturated, straight-chained or branched, acyclic alkyl group, a C$_3$–C$_7$ saturated cyclic alkyl group, or 1-methyl cyclohexene, provided that R is not a 2-propenyl group.

2. The compound according to claim 1, wherein R is a C$_3$–C$_7$ unsaturated, straight-chained or branched, acyclic alkyl group.

3. The compound according to claim 2, wherein R is selected from the group consisting of 2-methyl-2-propene, and 3-methyl-2-butene.

4. The compound according to claim 1, wherein R is a C$_3$–C$_7$ saturated cyclic alkyl group.

5. A fragrance composition comprising:
a compound having the formula

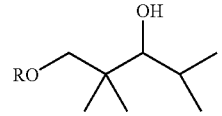

wherein R is a C$_1$–C$_7$ saturated, straight-chained or branched, acyclic or cyclic alkyl group or a C$_2$–C$_7$ unsaturated, straight-chain or branched, acyclic or cyclic alkyl group; and a carrier.

6. The fragrance composition according to claim 5, wherein R is a C$_1$–C$_7$ saturated, straight-chained or branched, acyclic alkyl group or a C$_2$–C$_7$ unsaturated, straight-chain or branched, acyclic alkyl group.

7. The fragrance composition according to claim 6, wherein R is selected from the group consisting of 2-methyl-2-propene, ethyl, 2-methylpropyl, and 3-methyl-2-butene.

8. The fragrance composition according to claim 5, wherein R is a $C_1$–$C_7$ saturated, straight-chained or branched, acyclic or cyclic alkyl group.

9. The fragrance composition according to claim 8, wherein said suitable carrier includes bleach.

10. A method of adding fragrance to a composition, comprising:
adding a suitable amount of a compound having the formula

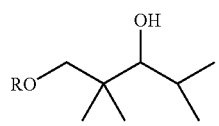

wherein R is a $C_1$–$C_7$ saturated, straight-chained or branched, acyclic or cyclic alkyl group or a $C_2$–$C_7$ unsaturated, straight-chained or branched, acyclic or cyclic alkyl group to a composition.

11. The method according to claim 10, wherein R is a $C_1$–$C_7$ saturated, straight-chained or branched, acyclic alkyl group or a $C_2$–$C_7$ unsaturated, straight-chained or branched, acyclic alkyl group.

12. The method according to claim 11, wherein R is selected from the group consisting of 2-methyl-2-propene, ethyl, 2-methylpropyl, and 3-methyl-2-butene.

13. The method according to claim 10, wherein R is a $C_1$–$C_7$ saturated, straight-chained or branched, acyclic or cyclic alkyl group.

14. The method according to claim 13, wherein said composition in need thereof includes bleach.

15. A method for making a compound having the formula,

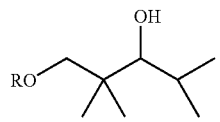

wherein R is a Ci–$C_7$ saturated, straight-chained or branched, acyclic or cyclic alkyl group, or a $C_2$–$C_7$ unsaturated, straight-chained or branched, acyclic or cyclic alkyl group, provided that R is not a 2-propenyl group, comprising:
contacting a 2,2,4-trimethyl-1,3-diol with a compound having the formula R'—X, wherein R' is a $C_1$–$C_7$ saturated, straight-chained or branched, acyclic or cyclic alkyl group, or a $C_2$–$C_7$ unsaturated, straight-chained or branched, acyclic or cyclic alkyl group provided that R is not a 2-propenyl group, X is a leaving group, in the presence of aqueous NaOH at a temperature suitable to cause a reaction in the resulting reaction mixture.

16. The method according to claim 15, wherein:
said temperature is at least 50° C.; and X is a halogen.

17. The method according to claim 15, further comprising: adding an alkylammonium salt to said reaction mixture.

18. The method according to claim 15, wherein R is a $C_1$–$C_7$ saturated, straight-chained or branched, acyclic alkyl group, Of or a $C_2$–$C_7$ unsaturated, straight-chain or branched, acyclic alkyl group.

19. The method according to claim 15, wherein R is selected from the group consisting of 2-methyl-2-propene, ethyl, 2-methylpropyl, and 3-methyl-2-butene.

20. The method according to claim 15, wherein R is a $C_1$–$C_7$ saturated, straight-chained or branched, acyclic or cyclic alkyl group.

21. A fragrance composition comprising a compound having the formula

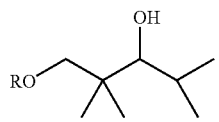

wherein R is a $C_1$–$C_7$ saturated, straight-chained or branched, acyclic or cyclic alkyl group, or a or a $C_2$–$C_7$ unsaturated, straight-chained or branched, acyclic or cyclic alkyl group provided that R is not a 2-propenyl group, in combination with at least one of a carrier and an additional perfumery material.

22. The fragrance composition according to claim 21, further comprising a surfactant to form a product, whereby said product is effective to act as at least one of a shampoo, conditioner, perfume, cologne, hair cream, pomade, hair cosmetic material, other cosmetic materials or cosmetic cleansers, room fragrance, soap, dishwashing detergent, laundry detergent, softener, disinfecting cleaning agent, deodorizing cleaning agent, furniture care material, disinfectant, bactericidal agent, repellant, bleaching agent, and other sanitation cleaning agents, toothpaste, moushwash, toilet paper and odor giving agents to aid in the taking of medication.

23. The compound according to claim 1, wherein R is a $C_4$–$C_5$ unsaturated, straight-chained or branched, acyclic alkyl group.

* * * * *